(12) United States Patent
Chew

(10) Patent No.: US 8,568,370 B2
(45) Date of Patent: Oct. 29, 2013

(54) INTRAVENOUS DRIP SET CONTROLLER WITH FLUSHER

(75) Inventor: Heng Hai Chew, Penang (MY)

(73) Assignee: Mecha-Medic Solution Sdn. Bhd., Penang (MY)

( * ) Notice: Subject to any disclaimer, the term of this patent is extended or adjusted under 35 U.S.C. 154(b) by 913 days.

(21) Appl. No.: 12/227,342

(22) PCT Filed: Apr. 20, 2007

(86) PCT No.: PCT/MY2007/000024
§ 371 (c)(1),
(2), (4) Date: Nov. 14, 2008

(87) PCT Pub. No.: WO2007/133061
PCT Pub. Date: Nov. 22, 2007

(65) Prior Publication Data
US 2009/0312719 A1    Dec. 17, 2009

(30) Foreign Application Priority Data
May 15, 2006    (MY) .............................. PI 2006 2216

(51) Int. Cl.
*A61M 5/00*    (2006.01)
*A61M 5/14*    (2006.01)
*F16K 7/04*    (2006.01)

(52) U.S. Cl.
USPC ............... 604/248; 251/6; 604/246; 604/249; 604/250; 604/251; 604/256

(58) Field of Classification Search
USPC ......... 604/251, 185, 246, 250, 248, 249, 256; 251/6, 8
See application file for complete search history.

(56) References Cited

U.S. PATENT DOCUMENTS

| | | | | |
|---|---|---|---|---|
| 4,335,866 A | * | 6/1982 | Bujan | 251/9 |
| 5,318,546 A | * | 6/1994 | Bierman | 604/250 |
| 6,422,529 B1 | * | 7/2002 | Adelberg | 251/6 |

* cited by examiner

*Primary Examiner* — Emily Schmidt
*Assistant Examiner* — Shefali Patel
(74) *Attorney, Agent, or Firm* — Brinks Hofer Gilson & Lione

(57) ABSTRACT

A regulating device for an intravenous drip set comprising a main housing unit (1) which comprises a mobile roller (2) which can gradually compress a flexible tubing (4) until the tubing (4) is fully compressed and a fixed roller (3) which together with the mobile roller (2) squeeze the flexible tubing of an intravenous line into a totally closed position to act as a flusher for the intravenous line, whereby when by sliding the entire device downwards along the tubing (4) proximally towards a patient, flushing of fluid in the intravenous line is thereby achieved.

7 Claims, 5 Drawing Sheets

INTRAVENOUS DRIP SET CONTROLLER WITH FLUSHER

RELATED APPLICATIONS

The present application is a 35 U.S.C. §371 national stage filing of International Patent Application No. PCT/MY/000024, filed Apr. 20, 2007, to which priority is claimed under 35 U.S.C. §120 and through which priority is claimed under 35 U.S.C. §119 to Malaysian Priority Patent Application No. PI2006-2216, filed May 15, 2006.

FIELD OF THE INVENTION

This invention relates to an intravenous drip set, and more particularly it relates to an improved monitoring device for controlling the flow and flushing the fluid.

BACKGROUND OF THE INVENTION

Intravenous drips are commonly used to administer a continuous flow of fluid to a patient for a predetermined length of time. The intravenous drip set generally includes a bag or container of intravenous fluid that is connected through a series of conduits comprising of flexible tubing, chambers and monitoring devices to a cannula inserted into a vein of the patient. The bag or container is supported at a higher elevation than the patient, so that the intravenous fluid flows down through the conduits by the force of gravity.

The drips are checked at regular intervals by nursing staff to ensure that the drip is working properly at all times and that the fluid is flowing into the patient at the correct rate. Such intravenous infusion systems have to be faithfully monitored by the nurse, to confirm that the delivery is not interrupted; that complete emptying does not take place; and that administration does not occur at a rate different from the prescribed rate. This would result, in the first case in an unnecessary lengthening of administration time; in the second case, the drawing of blood into the tube because its pressure is no longer opposed by that of the drip liquid; and in the third case, delivery at a rate other than the prescribed rate may have harmful consequences to the patient and his treatment.

Therefore, regulating the rate of flow through the intravenous drip set into the patient to achieve a desired or necessary rate of infusion of the fluid is essential and sometimes critical to successful patient treatment. It is also necessary, at regular intervals, to flush the system to achieve the optimum result and prolonging the use of the peripheral line.

To maintain a peripheral line flow, it is important to ensure that the flow of the liquid is always in good condition. In prior art devices, this is normally achieved by flushing with an additional syringe, drawing the fluid from the intravenous line and flushing it back inside. However this process of repeated punctuating of the line increases the risk of infection to the patient and increases the cost of having to replace every time with sterile syringes. Flushing is usually done when the flow is found to be decreasing and in order to maintain the desired flow. It is also done prior to an operation, to ensure that the flow of the medication during operation is uninterrupted. Flushing is also carried out preferably before intravenous medication is infused to prevent extravasation and after intravenous medication, to ensure the medication flows properly into the blood stream.

Prior art devices include expensive and sophisticated machines which are attached to the intravenous line separately and controlled either mechanically or electronically to monitor and regulate the flow as well as perform the flushing function. These devices are designed to be shared, when in use, and are not available for use, every time, on every intravenous line as that would be inconvenient, as well as uneconomical to do so. In most establishments, it is not possible to attach these devices on every intravenous line in use, as a result of which manual flushing is generally carried out.

Conventional methods of manual flushing which includes the use of the syringe, also may be attempted by simply increasing the flow of the intravenous drip by adjusting the regulator to provide a wider opening, or in most cases by the nurse simply milking the intravenous device by twirling the tube round her fingers and compressing the tube by squeezing the fluid proximally towards the patient, especially when getting additional syringes would be unavailable or inconvenient.

There is therefore a need for a simple, economical yet efficient in-built device that can perform both the task of regulating as well as flushing the intravenous line that can automatically be incorporated into every intravenous set in use.

SUMMARY OF THE INVENTION

It is a primary object of the present invention to provide for a built in device in the intravenous drip that can not only regulate the flow but also include a simple and efficient flushing mechanism for the intravenous line. This will facilitate an easy, efficient and regular flushing procedure to be carried out anytime, anywhere on every intravenous line.

By constantly flushing the intravenous line, it will extend and prolong the life span of any peripheral line and thus minimize the need for setting up another peripheral line. This will in turn help to minimize the extra risk of infection due to the setting up of the peripheral lines repeatedly. When an individual peripheral line's life span is prolonged, it is possible to obviate the need for a central line and venous cut down. which are more invasive and may put the patient's life at risk.

In short, this device will save time and cost by eliminating the use of syringes for flushing purposes and thereby decreasing the cost needed for setting up of repeated intravenous lines required in each particular case, as well as decreasing generally the rate of morbidity and mortality, which may arise as a complication of the more invasive use of venous cut downs and central lines. It is another object of the present invention to provide an intravenous set flow regulator cum flusher that is both simple to use, reliable and cheap to manufacture.

The present invention relates to a regulating device for an intravenous drip set which is attached on to the tubing of the intravenous drip line in between the bag and the cannula comprising of a main housing unit with the flexible tubing threaded through its entire length, wherein it comprises of two rollers:—

(a) a mobile roller which can rotate along a grove and rail within the body of the main housing, such that as it slides diagonally along the tubing, from one end to the other, it gradually compresses the flexible tubing until the tube is fully compressed and thereby functions as a regulator by adjusting the mobile roller at different positions on the main housing, (b) a fixed roller which rotates on its own axis and together with the mobile roller, engaging the flexible tubing on either side, and squeezing the flexible tubing of the intravenous line into a totally closed position to act as a flusher for the intravenous line, whereby when by sliding the entire unit downwards along the tubing proximally pushing the fluid in the intravenous line towards the patient, the flushing of the fluid in the intravenous line is thereby achieved.

Other objects and advantages of the present invention will become apparent from the following description taken in connection with the accompanying drawings, wherein is set for the by way of illustration and example, the preferred embodiments of the present invention and the best mode currently known to the inventor for carrying out the present invention.

The present invention comprises of certain novel features and combination of parts hereinafter fully described and illustrated in the accompanying drawings describing, in detail, the methods of the present invention. The invention described and claimed herein is not limited in scope by the specific embodiments herein disclosed, since these embodiments are intended as illustrations of several aspects of the present invention.

Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

DESCRIPTION OF THE PREFERRED EMBODIMENT

The present invention relates to a device that functions both as a built in regulator and a flusher for an intravenous drip set. It is attached to the flexible tubing and situated in between the bag and the cannula.

Figure 1A:
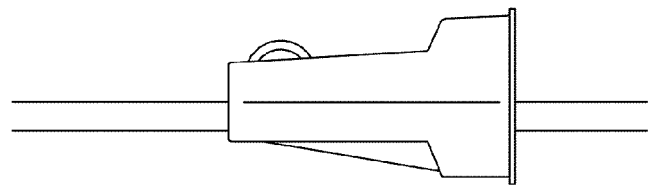
FIG. 1A illustrates a conventional drip regulator, most commonly used in prior art, showing its location on the tubing of the intravenous line.

FIG. 1A shows a conventional intravenous drip regulator, found in prior art, which comprises of a main housing with a mobile roller affixed within. The mobile roller slides diagonally on the intravenous line as it rotates along a groove and rail, all held within the housing, such that as it slides, it gradually compresses the flexible tubing thereby acting as a regulator as it moves along in different positions from one end to the other of the main housing.

Figure 1B:
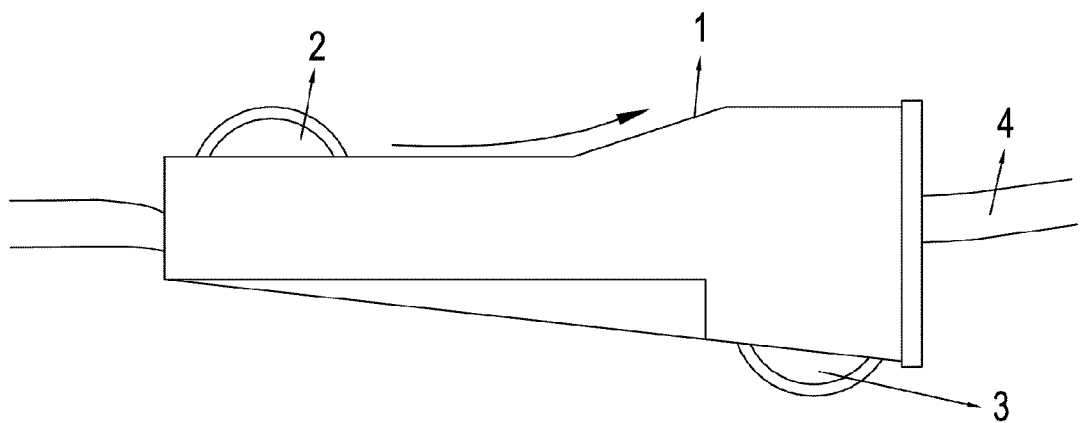
FIG. 1B illustrates the present invention of a regulator with a flusher showing its location on the tubing of the intravenous line.

FIG. 1 B shows the present invention, which comprises of a main housing (1) with a mobile roller (2) affixed within a main housing (1), to act as a regulator, it further comprises a fixed roller (3) attached to one end of the main housing (1). The fixed roller rotates on its own axis and together with the mobile roller (2) squeezes the flexible tubing of the intravenous line (4) into a totally closed position to act as a flusher for the intravenous line (4). The main housing (1) is preferably tapered towards one end, with the fixed roller (3) affixed at the larger upper end of the housing (1). The flexible tubing (4) is threaded through the entire length of the main housing (1) with the two rollers (2,3) engaged on either side. The main housing (1) serves also as a handle for gripping the device when performing the flushing action. To use the flushing function of the device, the mobile roller (2) should be pushed to meet the fixed roller (3), which is preferably located beyond the fully open position of the regulator. By holding the main housing (1), in this position, with the tubing (4) fully compressed between the rollers (2,3) and by sliding the entire unit downwards along the tubing (4) proximally pushing the fluid towards the patient, the flushing of the fluid in the intravenous line (4) is hereby achieved.

Figure 2A:
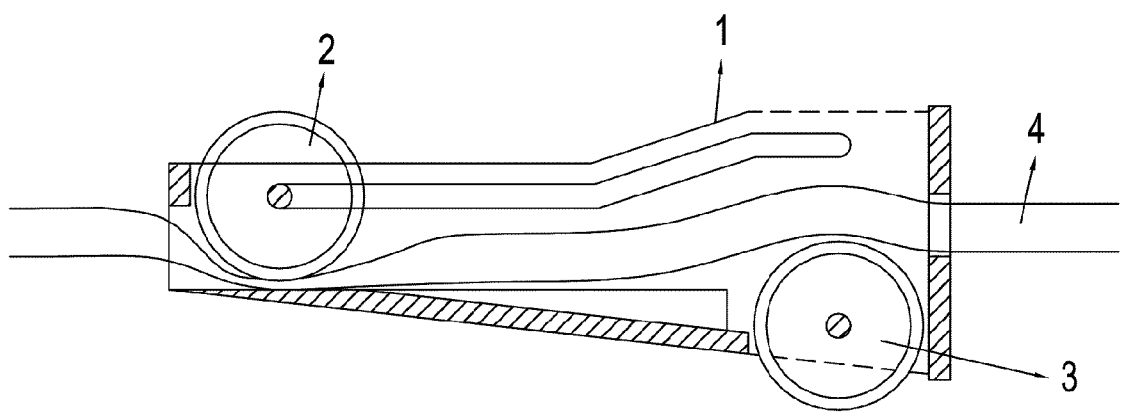
FIG. 2A illustrates a cross-sectional view of the present invention, in use, functioning as a regulator in its closed position, on the tubing of the intravenous line.
Figure 2B:
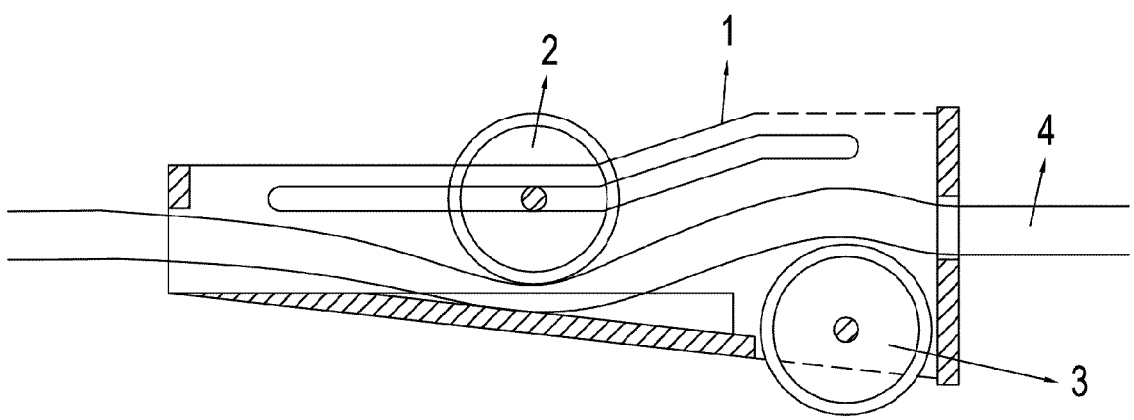
FIG. 2B illustrates a cross-sectional view of the present invention with its regulator, in use, in an intermediate position on the tubing of the intravenous line.
Figure 2C:
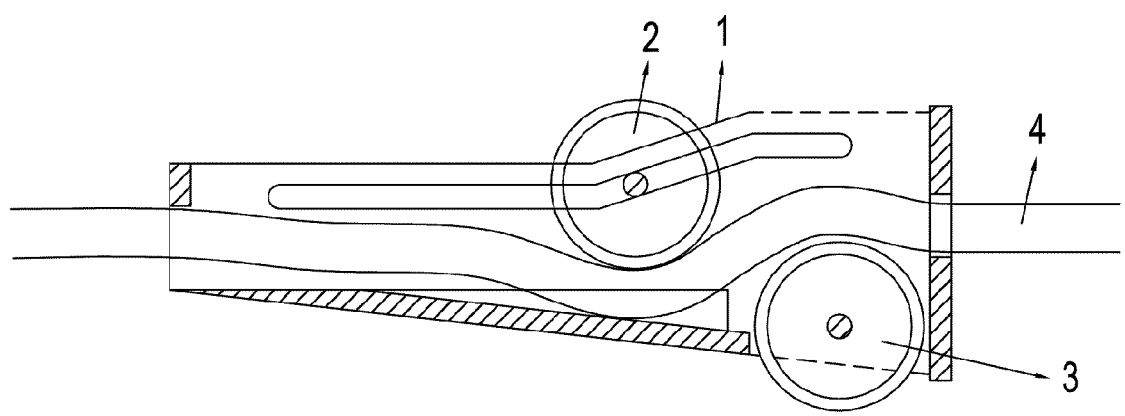
FIG. 2C illustrates a cross-sectional view of the present invention with its regulator, in use, in an open position on the tubing of the intravenous line.
Figure 3:
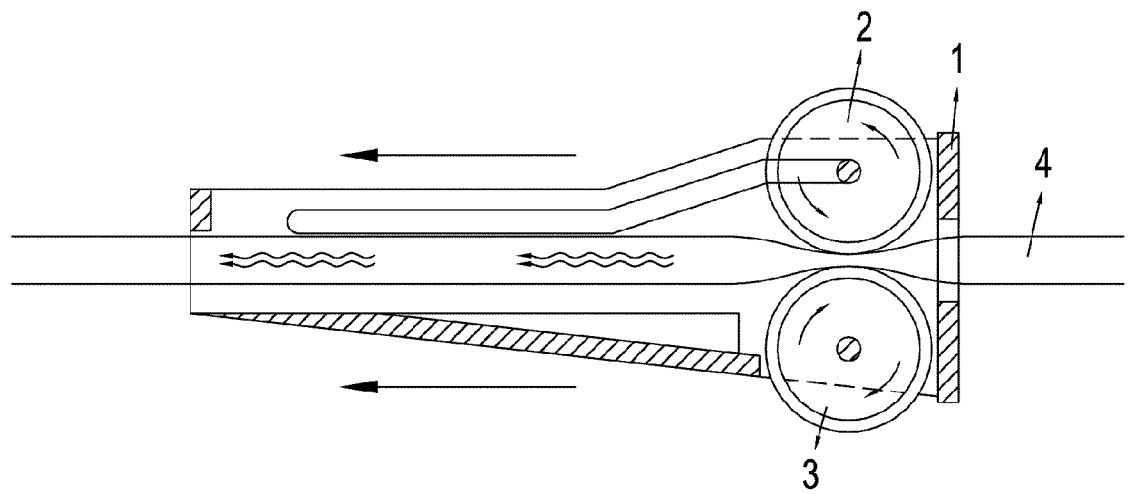
FIG. 3 illustrates a cross-sectional view of the present invention, in use, functioning as a flusher, on the tubing of the intravenous line.

FIG. 2A shows the initial position, when the device is used solely as regulator, with the mobile roller (2) set at the lower smaller end of the housing (1), squeezing the intravenous line (4) to a totally closed position, and with the fixed roller (3) affixed permanently at the other larger upper end of the main housing (1) FIG. 2B shows an intermediate position, when the device is used solely as a regulator with the mobile roller (2) in the middle position moving towards a maximum open position of the intravenous line (4). FIG. 2C shows a final position, when the device is used solely as a regulator with the mobile roller (2) in the maximum open position. The tubing (4) is fully released and the fluid flows through the intravenous line (4) unrestricted. FIG. 3 shows the lock position, when the device is to be used as a flusher, with both rollers (2,3) positioned opposite each other, thereby completely squeezing the intravenous line (4). The intravenous line's (4) lumen is now completely occluded. At this juncture, the whole device is gripped and pulled downwards proximally towards the patient, causing the fluid to be squeezed downwards as the rollers (2,3) both rotate simultaneously, on their own axes, in opposite directions, as shown by the direction of the arrows, with the tubing (4) squeezed in between them, as they slide downwards together, forcing the fluid downwards and towards the patient.

The invention claimed is:
1. A flow regulating device for an intravenous drip set which is attached on to a flexible tubing of an intravenous drip line in between a bag and a cannula comprising a main housing unit having an entire length with the flexible tubing, which comprises a portion of the intravenous line, threaded through the entire length of the main housing unit, the main housing unit further comprising:
   a mobile roller which can rotate and slide along a groove provided within the main housing unit such that as the mobile roller slides diagonally along the groove from one end to another end, the mobile roller gradually compresses the flexible tubing that is threaded through the entire length of the main housing unit until the flexible tubing is fully compressed and thereby fluid flow through the flexible tubing is regulated by adjusting a position of the mobile roller along the groove provided in the main housing unit; and
   a fixed roller which rotates on an axis that is in a fixed position within the main housing unit,
   the fixed roller and the mobile roller being provided on opposite sides of the flexible tubing within the main housing unit whereby the mobile roller can be positioned along the groove so that the flexible tubing is squeezed between the fixed roller and the mobile roller into a totally closed position to act as a flusher, for the intravenous line, whereby when by sliding the regulat- ing device along the tubing in one direction allows for flushing of fluid in the intravenous line.

2. The flow regulating device as claimed in claim 1, wherein the main housing unit is tapered towards an end thereof, and the fixed roller is affixed at a larger end of the main housing unit.

3. The flow regulating device as claimed in claim 2, wherein the fixed roller is located beyond a position at which when the mobile roller is located at the position the flexible tubing is fully opened.

4. The flow regulating device as claimed in claim 1, wherein the fixed roller is located beyond a position at which when the mobile roller is located at the position the flexible tubing is fully opened.

5. The flow regulating device as claimed in claim 1, wherein the main housing unit comprises a handle for gripping the regulating device when performing the flushing of the fluid in the intravenous line.

6. A flow regulating device for an intravenous drip set which comprises:
- a main housing unit having a length, opposite side walls, grooves formed in the opposite side walls and a passageway through which a flexible tubing can be threaded;
- a mobile roller on one side of the passageway which can rotate and move along the grooves, said grooves being configured so that as the mobile roller moves diagonally along at least a portion of the grooves, the mobile roller can gradually compress a length of the flexible tubing that is threaded through the passageway until the flexible tubing is fully compressed and thereby fluid flow through the flexible tubing is regulated by adjusting a position of the mobile roller along the grooves; and
- a fixed roller provided on an opposite side of the passageway from the mobile roller, wherein the fixed roller rotates on an axis that is in a fixed position within the main housing unit, wherein the mobile roller can be positioned along the grooves so that the flexible tubing threaded through the passageway can be squeezed between the fixed roller and the mobile roller into a totally closed position and the mobile roller and fixed roller can roll together along the flexible tubing as the mobile roller and fixed roller rotate about their axes.

7. A flow regulating device for an intravenous drip set which comprises:
- a main housing unit having a length, opposite side walls, grooves formed in the opposite side walls and a passageway through which a flexible tubing can be threaded;
- a mobile roller which can rotate and move along the grooves, said grooves being configured so that as the mobile roller moves diagonally along at least a portion of the grooves, the mobile roller gradually constricts the flexible tubing; and
- a fixed roller which rotates on an axis that is in a fixed position within the main housing unit, wherein the mobile roller and the fixed roller are located on opposite sides of the passageway and the mobile roller can be positioned along the grooves so as to be positioned directly across the passageway from the fixed roller so as to compress and close off a length of the flexible tubing positioned between the mobile roller and fixed roller.

\* \* \* \* \*